US006827925B1

US 6,827,925 B1

(12) United States Patent
Williams et al.

(10) Patent No.: US 6,827,925 B1
(45) Date of Patent: Dec. 7, 2004

(54) SPECIFIC BINDING PROTEINS INCLUDING ANTIBODIES WHICH BIND TO THE NECROTIC CENTER OF TUMORS, AND USES THEREOF

(75) Inventors: Andrew James Williams, Royston (GB); Philip Ronald Tempest, West Wratting (GB); Thor Las Holtet, Soborg (DK); Helen Jackson, North Hill (GB)

(73) Assignee: Cambridge Antibody Technology Limited, Cambridgeshire (GB)

( * ) Notice: Subject to any disclaimer, the term of this patent is extended or adjusted under 35 U.S.C. 154(b) by 0 days.

(21) Appl. No.: 09/720,493

(22) PCT Filed: Jul. 2, 1999

(86) PCT No.: PCT/GB99/02123

§ 371 (c)(1),
(2), (4) Date: Sep. 27, 2001

(87) PCT Pub. No.: WO00/01822

PCT Pub. Date: Jan. 13, 2000

(30) Foreign Application Priority Data

Jul. 2, 1998 (GB) .............................................. 9814383

(51) Int. Cl.$^7$ ........................ A61K 51/00; A61M 36/14
(52) U.S. Cl. .................... 424/1.49; 424/1.11; 424/1.65; 424/9.1; 424/9.2; 424/133.1; 424/155.1; 424/809; 530/387.1; 530/387.2; 530/388.21
(58) Field of Search .............................. 424/1.11, 1.49, 424/1.65, 1.69, 9.1, 9.6, 9.2, 133.1, 130.1, 138.1, 135.1, 144.1, 142.5, 155.1, 152.1, 146.1, 174.1, 800–809, 178.1, 1.73; 514/16; 536/22.1; 530/387.1, 328, 388.21, 387.3, 388.1, 389.1

(56) References Cited

U.S. PATENT DOCUMENTS

| | | | |
|---|---|---|---|
| 4,331,647 | A | 5/1982 | Goldenberg |
| 4,361,544 | A | 11/1982 | Goldenberg |
| 4,460,559 | A | 7/1984 | Goldenberg |
| 5,019,368 | A * | 5/1991 | Epstein et al. ............. 424/1.49 |
| 6,017,514 | A | 1/2000 | Epstein et al. |

FOREIGN PATENT DOCUMENTS

EP 0 270 340 10/1994

OTHER PUBLICATIONS

Database EMBL, PIR2: "Accession No: S19663" Residues 1–109, XP002119494 (1993).
Database EMBL EMHUM3: "Accession No: Z14195, entry Hse54427" Residues 1–434 XP002119495 (1993).
Miller et al., "Immunologic and Biochemical Analysis of TNT–1 TNT–2 Monoclonal Antibody Binding to Histones," *Hybridoma*, 12:689–98, XP002119491 cited in the application, (1993).
Database EMBL. PIR2: "Accession No: S47184" Residues 1–109, XP002119493 (1995).
Desrues et al., "Monclonal Antibody Po66 Uptake by Human Lung Tumours Implanted in Nude Mice: Effect of Co–Administration With Doxorubicin," *British Journal of Cancer*, 72:1076–1082, XP002119492 (1995).
King et al., "Preparation and Preclinical Evaluation of Humanised A33 Immunoconjugates for Radioimmunotherapy," *British Journal of Cancer*, 72:1364–1372, XP002911796 (1995).
Akiyama et al., "Cell Proliferation Kinetics of Human Gastric Carcinoma—A Quantitative Study of PCNA Expression Using a Color Image Analysis System," Database Biosis Online! Biosciences Information Service, Philadelphia, PA, 30:113–119, XP002119497 (1995).
Epstein et al., "Radioimmunodetection of Necrotic Lesions in Human Tumors Using I–131 Labeled TNT–1 F(ab')$_2$ Monoclonal Antibody" Antibody, Immunoconjugates, and Radiopharmaceuticals, vol. 4, No. 2, 1991, pp. 151–161.
Hornick et al., "A new chemically modified chimeric TNT–3 monoclonal antibody directed against DNA for the radioimmunotherapy of solid tumors" Cancer Biotherapy and Radiopharmaceuticals, 13/4, 1998, 255–268.

* cited by examiner

Primary Examiner—Dameron L. Jones
(74) Attorney, Agent, or Firm—Knobbe, Martens, Olson & Bear, LLP

(57) ABSTRACT

Specific binding members, based on the third CDR of the antibody NHS76 (SEQ ID NO: 2) are provided, together with their use in methods of treatment and diagnosis.

25 Claims, 8 Drawing Sheets

Figure 3A:
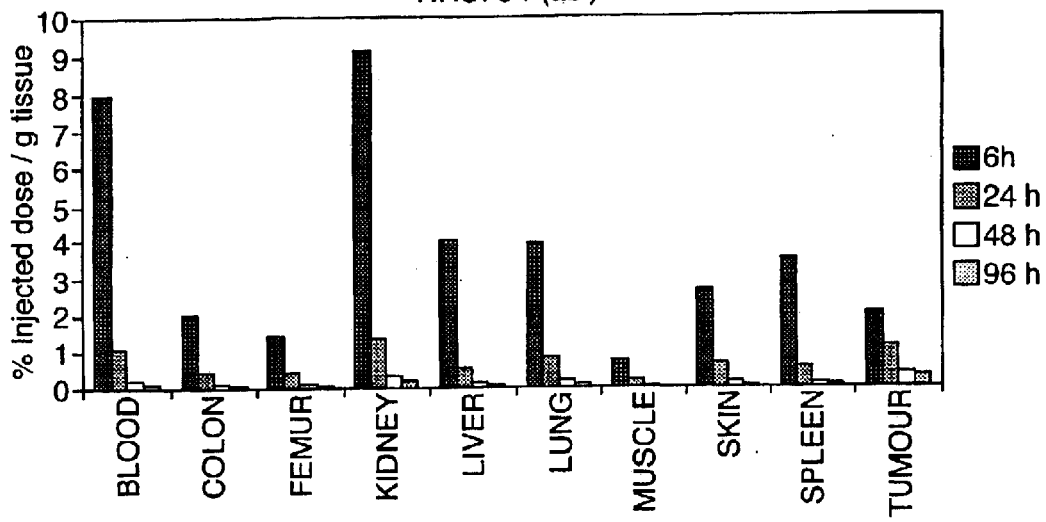

Fig. 1.

NHS76VH* Translated Sequence

Sequence Range: 1 to 351

```
         10        20        30        40        50        60
CAGGTGCAGCTGCAGGAGTCCGGCCCAGGACTGGTGAAGCCTTCGGAGACCCTGTCCCTC
GTCCACGTCGACGTCCTCAGGCCGGGTCCTGACCACTTCGGAAGCCTCTGGGACAGGGAG
  Q   V   Q   L   Q   E   S   G   P   G   L   V   K   P   S   E   T   L   S   L>    20
            TRANSLATION OF NHS76VH* [A]                    >

70        80        90       100       110       120
ACCTGCGCTGTCTCTGGTTACTCCATCAGCAGTGGTTACTACTGGGGCTGGATTCGGCAG
TGGACGCGACAGAGACCAATGAGGTAGTCGTCACCAATGATGACCCCGACCTAAGCCGTC
  T   C   A   V   S   G   Y   S   I   S  |S   G   Y   Y   W   G|  W   I   R   Q>  CDR1  40
            TRANSLATION OF NHS76VH* [A]                    >

130       140       150       160       170       180
CCCCCAGGGAAGGGGCTGGAGTGGATTGGGAGTATCTATCATAGTGGGAGCACCTACTAC
GGGGGTCCCTTCCCCGACCTCACCTAACCCTCATAGATAGTATCACCCTCGTGGATGATG
  P   P   G   K   G   L   E   W   I   G  |S   I   Y   H   S   G   S   T   Y   Y>  CDR2  60
            TRANSLATION OF NHS76VH* [A]                    >

190       200       210       220       230       240
AACCCGTCCCTCAAGAGTCGAGTCACCATATCAGTAGACACGTCCAAGAACCAGTTCTCC
TTGGGCAGGGAGTTCTCAGCTCAGTGGTATAGTCATCTGTGCAGGTTCTTGGTCAAGAGG
 |N   P   S   L   K   S|  R   V   T   I   S   V   D   T   S   K   N   Q   F   S>    80
            TRANSLATION OF NHS76VH* [A]                    >

250       260       270       280       290       300
CTGAAGCTGAGCTCTGTGACCGCCGCAGACACGGCCGTGTATTACTGTGCAAGAGGGAAG
GACTTCGACTCGAGACACTGGCGGCGTCTGTGCCGGCACATAATGACACGTTCTCCCTTC
  L   K   L   S   S   V   T   A   A   D   T   A   V   Y   Y   C   A   R  |G   K>  CDR3  100
            TRANSLATION OF NHS76VH* [A]                    >

310       320       330       340       350
TGGTCGAAGTTTGACTATTGGGGCCAAGGCACCCTGGTCACCGTCTCTTCA
ACCAGCTTCAAACTGATAACCCCGGTTCCGTGGGACCAGTGGCAGAGAAGT
  W   S   K   F   D   Y|  W   G   Q   G   T   L   V   T   V   S   S>
            TRANSLATION OF NHS76VH* [A]                    >
```

Fig.2.

**NHS76VL\* Translated Sequence**

Sequence Range: 1 to 324

```
         10        20        30        40        50        60
TCCTCTGAGCTGACTCAGGACCCTGCTGTGTCTGTGGCCTTGGGACAGACAGTCAGGATC
AGGAGACTCGACTGAGTCCTGGGACGACACAGACACCGGAACCCTGTCTGTCAGTCCTAG
  S   S   E   L   T   Q   D   P   A   V   S   V   A   L   G   Q   T   V   R   I>         20
              TRANSLATION OF NHS76VL* [A]                    >

70        80        90       100       110       120
ACATGCCAAGGAGACAGCCTCAGAAGCTATTATGCAAGCTGGTACCAGCAGAAGCCAGGA
TGTACGGTTCCTCTGTCGGAGTCTTCGATAATACGTTCGACCATGGTCGTCTTCGGTCCT
  T   C  |Q   G   D   S   L   R   S   Y   Y   A   S|  W   Y   Q   Q   K   P   G>  CDR1   40
              TRANSLATION OF NHS76VL* [A]                    >

130       140       150       160       170       180
CAGGCCCCTGTACTTGTCATCTATGGTAAAAACAACCGGCCCTCAGGGATTCCAGACCGA
GTCCGGGGACATGAACAGTAGATACCATTTTTGTTGGCCGGGAGTCCCTAAGGTCTGGCT
  Q   A   P   V   L   V   I   Y  |G   K   N   N   R   P   S|  G   I   P   D   R>  CDR2   60
              TRANSLATION OF NHS76VL* [A]                    >

190       200       210       220       230       240
TTCTCTGGCTCCAGCTCAGGAAACACAGCTTCCTTGACCATCACTGGGGCTCAGGCGGAA
AAGAGACCGAGGTCGAGTCCTTTGTGTCGAAGGAACTGGTAGTGACCCCGAGTCCGCCTT
  F   S   G   S   S   S   G   N   T   A   S   L   T   I   T   G   A   Q   A   E>         80
              TRANSLATION OF NHS76VL* [A]                    >

250       260       270       280       290       300
GATGAGGCTGACTATTACTGTAACTCCCGGGACAGCAGTGGTAACCATGTGGTATTCGGC
CTACTCCGACTGATAATGACATTGAGGGCCCTGTCGTCACCATTGGTACACCATAAGCCG
  D   E   A   D   Y   Y   C  |N   S   R   D   S   S   G   N   H   V   V|  F   G>  CDR3  100
              TRANSLATION OF NHS76VL* [A]                    >

310       320
GGAGGGACCAAGCTGACCGTCCTA
CCTCCCTGGTTCGACTGGCAGGAT
  G   G   T   K   L   T   V   L>
     TRANSLATION OF NH____>
```

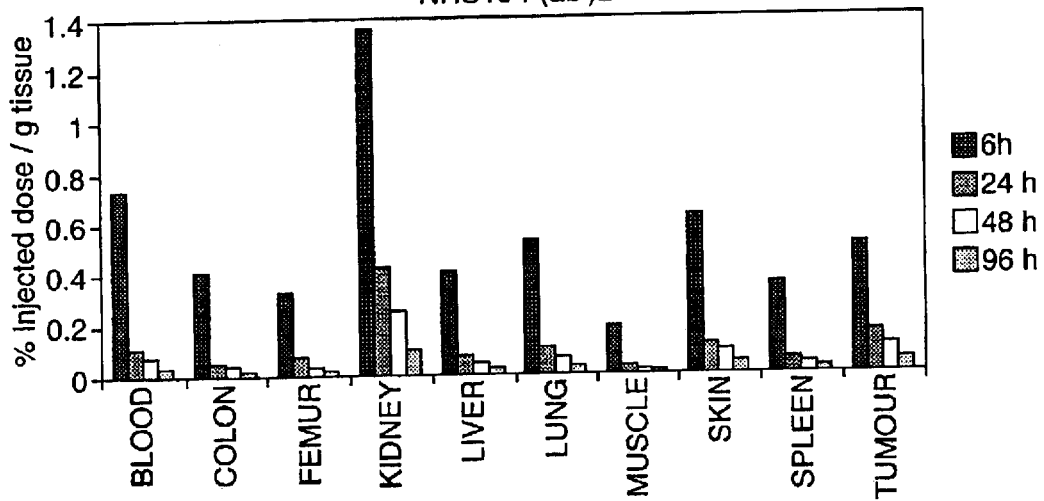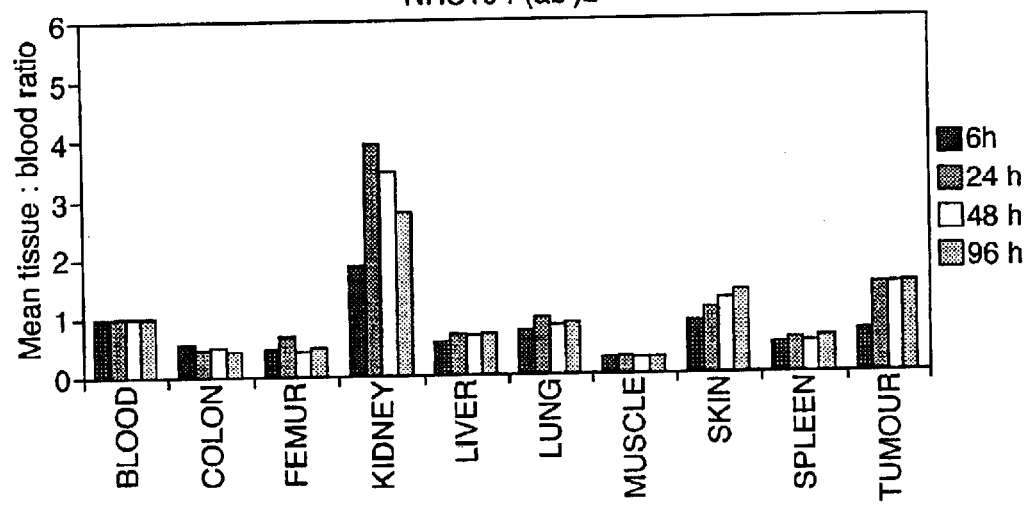

1 Raji (human)
2 NSO (mouse)
3 JTC-19 (rat)
4 JH4 (guinea pig)
5 Histone H1 (bovine)
6 Histone H2A (bovine)
7 Histone H2B (bovine)
8 Histone H3 (bovine)
9 Histone H4 (bovine)

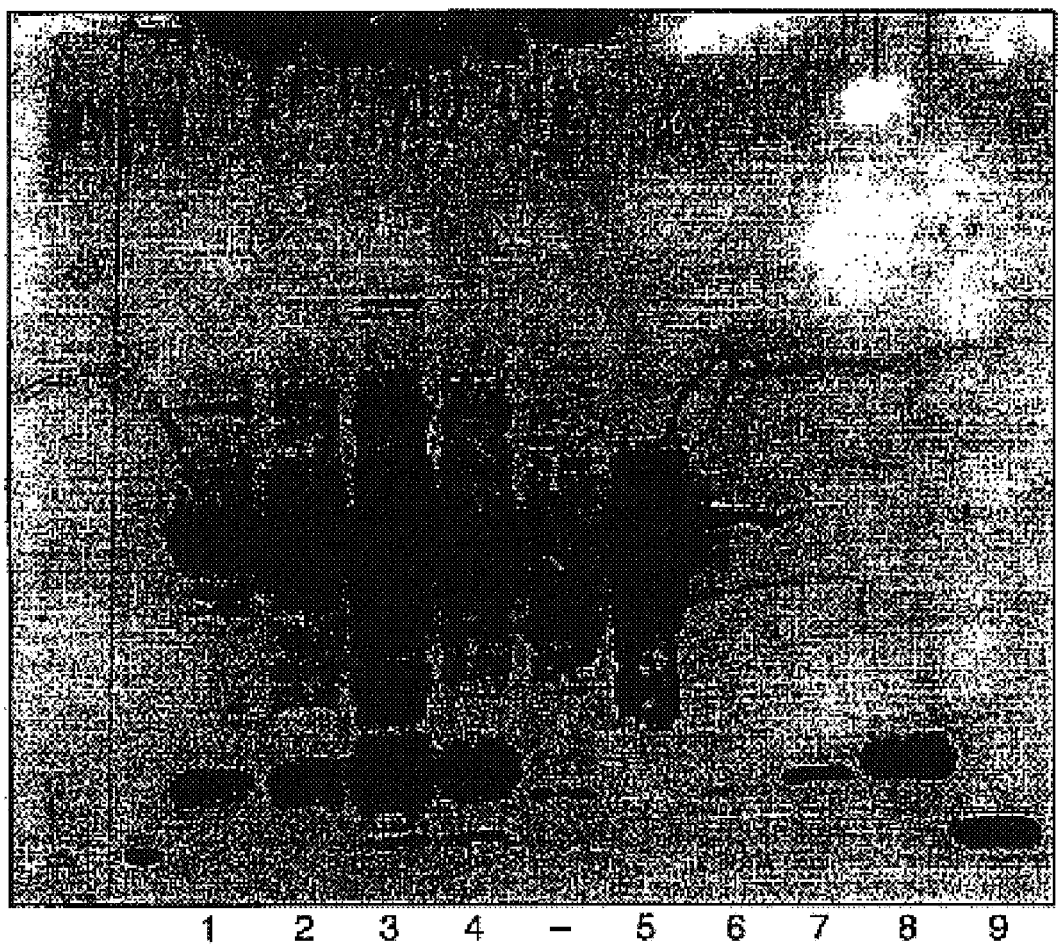

SEQUENCE LISTING

<160> NUMBER OF SEQ ID NOS: 22

<210> SEQ ID NO 1
<211> LENGTH: 351
<212> TYPE: DNA
<213> ORGANISM: Homo sapiens
<220> FEATURE:
<221> NAME/KEY: CDS
<222> LOCATION: (1)..(351)

<400> SEQUENCE: 1 cag gtg cag ctg cag gag tcc ggc cca gga ctg gtg aag cct tcg gag    48

```
Gln Val Gln Leu Gln Glu Ser Gly Pro Gly Leu Val Lys Pro Ser Glu
 1               5                  10                  15 acc ctg tcc ctc acc tgc gct gtc tct ggt tac tcc atc agc agt ggt      96
Thr Leu Ser Leu Thr Cys Ala Val Ser Gly Tyr Ser Ile Ser Ser Gly
             20                  25                  30 tac tac tgg ggc tgg att cgg cag ccc cca ggg aag ggg ctg gag tgg     144
Tyr Tyr Trp Gly Trp Ile Arg Gln Pro Pro Gly Lys Gly Leu Glu Trp
         35                  40                  45 att ggg agt atc tat cat agt ggg agc acc tac tac aac ccg tcc ctc     192
Ile Gly Ser Ile Tyr His Ser Gly Ser Thr Tyr Tyr Asn Pro Ser Leu
     50                  55                  60 aag agt cga gtc acc ata tca gta gac acg tcc aag aac cag ttc tcc     240
Lys Ser Arg Val Thr Ile Ser Val Asp Thr Ser Lys Asn Gln Phe Ser
 65                  70                  75                  80 ctg aag ctg agc tct gtg acc gcc gca gac acg gcc gtg tat tac tgt     288
Leu Lys Leu Ser Ser Val Thr Ala Ala Asp Thr Ala Val Tyr Tyr Cys
                 85                  90                  95 gca aga ggg aag tgg tcg aag ttt gac tat tgg ggc caa ggc acc ctg     336
Ala Arg Gly Lys Trp Ser Lys Phe Asp Tyr Trp Gly Gln Gly Thr Leu
             100                 105                 110 gtc acc gtc tct tca                                                  351
Val Thr Val Ser Ser
         115

<210> SEQ ID NO 2
<211> LENGTH: 117
<212> TYPE: PRT
<213> ORGANISM: Homo sapiens

<400> SEQUENCE: 2

Gln Val Gln Leu Gln Glu Ser Gly Pro Gly Leu Val Lys Pro Ser Glu
 1               5                  10                  15

Thr Leu Ser Leu Thr Cys Ala Val Ser Gly Tyr Ser Ile Ser Ser Gly
             20                  25                  30

Tyr Tyr Trp Gly Trp Ile Arg Gln Pro Pro Gly Lys Gly Leu Glu Trp
         35                  40                  45

Ile Gly Ser Ile Tyr His Ser Gly Ser Thr Tyr Tyr Asn Pro Ser Leu
     50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Lys Trp Ser Lys Phe Asp Tyr Trp Gly Gln Gly Thr Leu
             100                 105                 110

Val Thr Val Ser Ser
         115

<210> SEQ ID NO 3
<211> LENGTH: 324
<212> TYPE: DNA
<213> ORGANISM: Homo sapiens
<220> FEATURE:
<221> NAME/KEY: CDS
<222> LOCATION: (1)..(324)

<400> SEQUENCE: 3 tcc tct gag ctg act cag gac cct gct gtg tct gtg gcc ttg gga cag      48
Ser Ser Glu Leu Thr Gln Asp Pro Ala Val Ser Val Ala Leu Gly Gln
 1               5                  10                  15 aca gtc agg atc aca tgc caa gga gac agc ctc aga agc tat tat gca      96
Thr Val Arg Ile Thr Cys Gln Gly Asp Ser Leu Arg Ser Tyr Tyr Ala
```

```
Thr Val Arg Ile Thr Cys Gln Gly Asp Ser Leu Arg Ser Tyr Tyr Ala
            20                  25                  30 agc tgg tac cag cag aag cca gga cag gcc cct gta ctt gtc atc tat       144
Ser Trp Tyr Gln Gln Lys Pro Gly Gln Ala Pro Val Leu Val Ile Tyr
        35                  40                  45 ggt aaa aac aac cgg ccc tca ggg att cca gac cga ttc tct ggc tcc       192
Gly Lys Asn Asn Arg Pro Ser Gly Ile Pro Asp Arg Phe Ser Gly Ser
 50                  55                  60 agc tca gga aac aca gct tcc ttg acc atc act ggg gct cag gcg gaa       240
Ser Ser Gly Asn Thr Ala Ser Leu Thr Ile Thr Gly Ala Gln Ala Glu
 65                  70                  75                  80 gat gag gct gac tat tac tgt aac tcc cgg gac agc agt ggt aac cat       288
Asp Glu Ala Asp Tyr Tyr Cys Asn Ser Arg Asp Ser Ser Gly Asn His
                85                  90                  95 gtg gta ttc ggc gga ggg acc aag ctg acc gtc cta                       324
Val Val Phe Gly Gly Gly Thr Lys Leu Thr Val Leu
            100                 105
```

<210> SEQ ID NO 4
<211> LENGTH: 108
<212> TYPE: PRT
<213> ORGANISM: Homo sapiens

<400> SEQUENCE: 4

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105
```

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 5
agcggataac aatttcacac agg                                              23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
gtcgtctttc cagacgttag t                                                21

<210> SEQ ID NO 7
<211> LENGTH: 23

```
<212> TYPE: DNA
<213> ORGANISM: Artificial Sequence
<220> FEATURE:
<223> OTHER INFORMATION: Description of Artificial Sequence: Primer

<400> SEQUENCE: 7
agcggataac aatttcacac agg                                              23

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
ctcttctgag atgagttttt g                                                21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
accgccagag ccacctccgc c                                                21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
ggcggaggtg gctctggcgg t                                                21

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 11
ctaagcttac tgagcacaca ggacctcacc                                       30

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 12
aattttcgaa ctacagttac tgagcacaca ggacc                                 35

<210> SEQ ID NO 13
<211> LENGTH: 43
<212> TYPE: DNA
<213> ORGANISM: Artificial Sequence
<220> FEATURE:
<223> OTHER INFORMATION: Description of Artificial Sequence: Primer

<400> SEQUENCE: 13
```

```
atgggccctt ggtggaagct gaagagacgg tgaccagggt gcc         43
```

<210> SEQ ID NO 14
<211> LENGTH: 56
<212> TYPE: DNA
<213> ORGANISM: Artificial Sequence
<220> FEATURE:
<223> OTHER INFORMATION: Description of Artificial Sequence: Primer

<400> SEQUENCE: 14

```
gcaaagttaa ttaattctac tccacctagg acgtcagct tggtccctcc gccgaa    56
```

<210> SEQ ID NO 15
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 15

```
tttggatatc tctccacagg tgtccactcc caggtgcagc tgcaggagtc cggccca    57
```

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 16

```
ctggggctgg attcggcagc cccca       25
```

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17

```
tggggctgc cgaatccagc cccag       25
```

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 18

```
gccctcaggg attccagacc gattc       25
```

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 19

```
gaatcggtct ggaatccctg agggc       25
```

<210> SEQ ID NO 20
<211> LENGTH: 53
<212> TYPE: DNA
<213> ORGANISM: Artificial Sequence -continued

```
<220> FEATURE:
<223> OTHER INFORMATION: Description of Artificial Sequence: Primer

<400> SEQUENCE: 20
ttggatatct ctccacaggt gtccactcct cttctgagct gactcaggac cct          53

<210> SEQ ID NO 21
<211> LENGTH: 351
<212> TYPE: DNA
<213> ORGANISM: Homo sapiens

<400> SEQUENCE: 21
tgaagagacg gtgaccaggg tgccttggcc ccaatagtca aacttcgacc acttccctct    60
tgcacagtaa tacacggccg tgtctgcggc ggtcacagag ctcagcttca gggagaactg   120
gttcttggac gtgtctactg atatggtgac tcgactcttg agggacgggt tgtagtaggt   180
gctcccacta tgatagatac tcccaatcca ctccagcccc ttccctgggg gctgccgaat   240
ccagccccag tagtaaccac tgctgatgga gtaaccagag acagcgcagg tgagggacag   300
ggtctccgaa ggcttcacca gtcctgggcc ggactcctgc agctgcacct g            351

<210> SEQ ID NO 22
<211> LENGTH: 324
<212> TYPE: DNA
<213> ORGANISM: Homo sapiens

<400> SEQUENCE: 22
taggacggtc agcttggtcc ctccgccgaa taccacatgg ttaccactgc tgtcccggga    60
gttacagtaa tagtcagcct catcttccgc ctgagcccca gtgatggtca aggaagctgt   120
gtttcctgag ctggagccag agaatcggtc tggaatccct gagggccggt tgttttttacc  180 atagatgaca agtacagggg cctgtcctgg cttctgctgg taccagcttg cataatagct   240
tctgaggctg tctccttggc atgtgatcct gactgtctgt cccaaggcca cagacacagc   300
agggtcctga gtcagctcag agga                                         324
```

SPECIFIC BINDING PROTEINS INCLUDING ANTIBODIES WHICH BIND TO THE NECROTIC CENTER OF TUMORS, AND USES THEREOF

This application claims priority to PCT application number PCT/GB/99/02123, which was filed on Jul. 2, 1999, and claims a priority date of Jul. 7, 1998 based on all documents in the record.

The present invention relates to specific binding members, particularly antibodies and fragments thereof, which bind to the necrotic centres of tumours. These specific binding members are useful in the treatment of cancer.

BACKGROUND TO THE INVENTION

The treatment of proliferative disease, particularly cancer, by chemotherapeutic means often relies upon exploiting differences in target proliferating cells and other normal cells in the human or animal body. For example, many chemical agents are designed to be taken up by rapidly replicating DNA so that the process of DNA replication and cell division is disrupted. Another approach is to identify antigens on the surface of tumour cells which are not normally expressed in developed human tissue, such as embryonic antigens. Such antigens can be targeted with binding proteins such as antibodies to deliver a toxic agent to or other substance which is capable directly or indirectly of activating a toxic agent at, the site of a tumour.

An alternative approach which has been developed more recently relies on the fact that a significant proportion of tumour cells are in various stages of cell degeneration and death. Unlike programmed cell death (apoptosis) which occurs during the natural turnover of certain cell types, tumour cells undergo a degenerative and less controlled death during which they have been found to exhibit abnormal surface membrane permeability. European patent application EP-A-270340 describes the preparation of murine antibodies to nuclear components of cells which are able to target necrotic cells in a tumour by exploiting this phenomenon. Miller et al (Hybridoma, 1993, 12, 689–697) describe a particular antibody prepared in accordance with EP-A-270340. This antibody, TNT-1, was found to bind histone fraction H1. The histones are the most abundant proteins in chromatin, the concentration of each type of histone being approximately 5000 times higher than the concentration of a typical sequence-specific DNA-binding protein. Epstein et al (in "Handbook of Targeted Delivery of Imaging Agents" CRC press, Inc., 1995, ed. VP Torchilin) describes the uptake of radiolabelled TNT-1 into nude mice bearing the ME-180 cervical carcinoma, and report that there was no appreciable labelling of other organs. The authors also used the F(ab')$_2$ fragment of TNT-1 labelled with $^{131}$I for tumour imaging studies in human patients.

A known problem with the use of murine antibodies in human therapy is that repeat treatment of such antibodies leads to a human anti-mouse antibody (HAMA) response. HAMA responses have a range of effects, from neutralisation of the administered antibody leading to a reduced therapeutic dose, through to allergic responses, serum sickness and renal impairment. In order to overcome these disadvantages humanization of antibodies has been developed. More recently, repertoires of human antibodies have been cloned and these can be screened, for example by phage display technology, (McCafferty et al, WO92/01047) to identify human antibodies specific for human antigens.

DISCLOSURE OF THE INVENTION

We have investigated the binding properties of the TNT-1 antibody and attempted to secure human antibodies with similar binding profiles and useful tumour localisation in animal models. We have found that although TNT-1 binds primarily to nuclear histone H1 it also binds a complex pattern of other histones and non-identified proteins in a nuclear preparation. We were able to identify a number of human antibodies, screened primarily against a nuclear extract and further against histone H1 which had similar binding profiles. Despite the similarities in binding profiles between the human antibody clones analysed, only one (identified below as "NHS76") was found to additionally exhibit low cross reactivity to non-necrotic tissues and organs and good tumour:blood localisation ratio. Other candidate antibodies tested either showed cross-reactivity or had poorer tumour:blood ratios of localisation.

Accordingly, specific binding proteins such as antibodies which are based on the complementarity-determining regions (CDRs) of the NHS76 antibody identified, particularly the CDR 3 regions, will be useful for targeting the necrotic centres of malignant tumours.

In the accompanying drawings, the nucleic acid sequence and translation thereof of the NHS76 VH gene is shown in FIG. 1. The nucleic acid sequence is designated SEQ ID NO:1. The translation is SEQ ID NO:2. The VL gene of NHS 76 is shown as FIG. 2. Its nucleic acid sequence is designated SEQ ID NO:3, and its translation as SEQ ID NO:4. In both figures, the CDR's are indicated in boxes.

In a first aspect the present invention provides an isolated specific binding member capable of binding an intracellular antigen, wherein said specific binding member comprises a polypeptide binding domain comprising an amino acid sequence substantially as set out as residues 99 to 106 of SEQ ID NO:2. The invention further provides said isolated specific binding member which further comprises one or both of the polypeptide binding domains substantially as set out as residues 31–36 and 51–66 of SEQ ID NO:2, preferably both. In a preferred embodiment, the binding domains are carried by a human antibody framework. One example of such an embodiment is the sequence substantially as shown in SEQ ID NO:2.

In a second aspect, the invention provides an isolated specific binding member capable of binding an intracellular antigen, wherein said specific binding member comprises a polypeptide binding domain comprising an amino acid sequence substantially as set out as residues 88 to 98 of SEQ ID NO:4. The invention further provides said isolated specific binding member which further comprises one or both of the polypeptide binding domains substantially as set out as residues 23–33 and 49–55 of SEQ ID NO:4, preferably both. In a preferred embodiment, the binding domains are carried by a human antibody framework. One example of such an embodiment is the sequence substantially as shown in SEQ ID NO:4.

In a particularly preferred embodiment, the invention provides a specific binding member which comprises a first specific binding member comprising a sequence substantially as set out as residues 99 to 106 of SEQ ID NO:2 in association with a second specific binding member comprising a sequence substantially set out as residues 88 to 98 of SEQ ID NO:4. Such a specific binding member according to the invention may be in the form of an antibody F(ab')2 fragment.

Specific binding members of the invention may carry a detectable or functional label.

In further aspects, the invention provides an isolated nucleic acid which comprises a sequence encoding a specific binding member as defined above, and methods of preparing specific binding members of the invention which comprise expressing said nucleic acids under conditions to bring about expression of said binding member, and recovering the binding member.

Specific binding members according to the invention may be used in a method of treatment or diagnosis of the human or animal body, such as a method of treatment of a tumour in a human patient which comprises administering to said patient an effective amount of a specific binding member of the invention.

These and other aspects of the invention are described in further detail below.

DETAILED DESCRIPTION OF THE INVENTION

A. Terminology

Specific binding member

This describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

Antibody

This describes an immunoglobulin whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are the immunoglobulin isotypes and their isotypic subclasses; fragments which comprise an antigen binding domain such as Fab, scFv, Fv, dAb, Fd; and diabodies.

It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544–546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242, 423–426, 1988; Huston et al, PNAS USA, 85, 5879–5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444–6448, 1993).

Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

Where bispecific antibodies are to be used, these may be conventional bispecific antibodies, which can be manufactured in a variety of ways (Holliger, P. and Winter C. Current Opinion Biotechnol. 4, 446–449 (1993)), eg prepared chemically or from hybrid hybridomas, or may be any of the bispecific antibody fragments mentioned above. It may be preferable to use scFv dimers or diabodies rather than whole antibodies. Diabodies and scFv can be constructed without an Fc region, using only variable domains, potentially reducing the effects of anti-idiotypic reaction. Other forms of bispecific antibodies include the single chain "Janusins" described in Traunecker et al, EMBO Journal, 10, 3655–3659, (1991).

Bispecific diabodies, as opposed to bispecific whole antibodies, may also be particularly useful because they can be readily constructed and expressed in *E. coli*. Diabodies (and many other polypeptides such as antibody fragments) of appropriate binding specificities can be readily selected using phage display (WO94/13804) from libraries. If one arm of the diabody is to be kept constant, for instance, with a specificity directed against antigen X, then a library can be made where the other arm is varied and an antibody of appropriate specificity selected.

Antigen binding domain

This describes the part of an antibody which comprises the area which specifically binds to and is complementary to part or all of an antigen. Where an antigen is large, an antibody may only bind to a particular part of the antigen, which part is termed an epitope. An antigen binding domain may be provided by one or more antibody variable domains. Preferably, an antigen binding domain comprises an antibody light chain variable region (VL) and an antibody heavy chain variable region (VH).

Specific

This may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

Comprise

This is generally used in the sense of include, that is to say permitting the presence of one or more features or components.

Isolated

This refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Specific binding members may be glycosylated, either naturally or by systems of heterologous eukaryotic cells, or they may be (for example if produced by expression in a prokaryotic cell) unglycosylated.

B. Detailed Disclosure

Isolated specific binding members of the invention are those such as NHS76 which are capable of binding an intracellular antigen. In particular, the member will bind to human histone H1. However the NHS76 antibody which forms a particular aspect of the invention also shows a pattern of reactivity to a range of intracellular antigens. It is preferred that other binding members of the invention also show the same or substantially similar pattern reactivity. This may be determined by comparing such members with an antibody comprising the VH and VL domains shown in SEQ ID NO:2 and SEQ ID NO:4 respectively. The comparison will typically be made using a western blot in which binding members are bound to duplicate blots prepared from a nuclear preparation of cells so that the pattern of binding can be directly compared. Suitable nuclear preparations and conditions for western blotting are described below in the accompanying examples.

In particular, NHS76 shows differential binding to histones. This is reflected in the ELISA data of histone binding (Example 7 below) which shows that NHS shows greatest binding to histone H1 followed by H3>H2B>H2A, H4. Suitable western blot conditions for measurement of binding to histones are illustrated in the accompanying examples.

As outlined above, we have found that the NHS76 antibody has in vivo properties which are not shared by other antibodies with apparently similar binding profiles. While not wishing to be bound by any one particular theory, one explanation for this is that the specific antibody-antigen interaction of the antibody results in the unexpectedly desirable in vivo activity. The binding of an antibody co its target antigen is mediated through the CDRs of its heavy and light chains, with the role of CDR3 being of particular importance. Accordingly, specific binding members based on the CDR3 regions of the heavy or light chain, and preferably both, of NHS76 will be useful specific binding members for in vivo therapy.

In general, the CDR3 regions, comprising amino acid sequences substantially as set out as residues 99 to 106 of SEQ ID NO:2 and 88 to 98 of SEQ ID NO:4 will be carried in a structure which allows for binding of the CDR3 regions to an intracellular antigen.

By "substantially as set out" it is meant that the CDR3 regions of the invention will be either identical or highly homologous to the specified regions of SEQ ID NO:2 and SEQ ID NO:4. By "highly homologous" it is contemplated that from 1 to 5, preferably from 1 to 4 such as 1 to 3 or 1 or 2 substitutions may be made in the CDRs.

The structure for carrying the CDR3s of the invention will generally be of an antibody heavy or light chain sequence or substantial portion thereof in which the CDR3 regions are located at locations corresponding to the CDR3 region of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. (US Department of Health and Human Services, 4$^{th}$ Edition, 1987, and updates thereof, which are now available on the Internet).

Preferably, the amino acid sequence substantially as set out as residues 99 to 106 of SEQ ID NO:2 is carried as the CDR3 in a human heavy chain variable domain or a substantial portion thereof, and the amino acid sequence substantially as set out as residues 88 to 98 of SEQ ID NO:4 is carried as the CDR3 in a human light chain variable domain or a substantial portion thereof.

The variable domains may be derived from any germline or rearranged human variable domain, or may be a synthetic variable domain based on consensus sequences of known human variable domains. The CDR3-derived sequences of the invention, as defined in the preceding paragraph, may be introduced into a repertoire of variable domains lacking CDR3 regions, using recombinant DNA technology.

For example, Marks et al (*Bio/Technology*, 1992, 10:779–783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide specific binding members of the invention. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members.

Analogous shuffling or combinatorial techniques are also disclosed by Stemmer (*Nature*, 1994, 370:389–391), who describes the technique in relation to a β-lactamase gene but observes that the approach may be used for the generation of antibodies.

A further alternative is to generate novel VH or VL regions carrying the CDR3-derived sequences of the invention using random mutagenesis of, for example, the NHS76 VH or VL genes to generate mutations within the entire variable domain. Such a technique is described by Gram et al (1992, *Proc. Natl. Acad. Sci., USA*, 89:3576–3580), who used error-prone PCR.

Another method which may be used is to direct mutagenesis to CDR regions of VH or VL genes. Such techniques are disclosed by Barbas et al, (1994, *Proc. Natl. Acad. Sci., USA*, 91:3809–3813) and Schier et al (1996, *J. Mol. Biol.* 263:551–567).

All the above described techniques are known as such in the art and in themselves do not form part of the present invention. The skilled person will be able to use such techniques to provide specific binding members of the invention using routine methodology in the art.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of—or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as discussed in more detail below.

Although in a preferred aspect of the invention specific binding members comprising a pair of binding domains based on sequences substantially set out in SEQ ID NO:2 and SEQ ID NO:4 are preferred, single binding domains based on either of these sequences form further aspects of the invention. In the case of the binding domains based on the sequence substantially set out in SEQ ID NO:2, such binding domains may be used as targeting agents for intracellular antigens since it is known that immunoglobulin VH domains are capable of binding target antigens in a specific manner. In the case of either of the single chain specific binding domains, these domains may be used to screen for complementary domains capable of forming a two-domain specific binding member which has in vivo properties as good as or equal to the NHS 76 antibody disclosed herein.

This may be achieved by phage display screening methods using the so-called hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid.

Specific binding members of the present invention may further comprise antibody constant regions or parts thereof. For example, specific binding members based on SEQ ID NO:4 may be attached at their C-terminal end to antibody light chain constant domains including human Cκ or Cλ chains, preferably Cλ chains. Similarly, specific binding members based on SEQ ID NO:2 may be attached at their C-terminal end to all or part of an immunoglobulin heavy chain derived from any antibody isotype, e.g. IgG, IgA, IgE and IgM and any of the isotype sub-classes, particularly IgG1 and IgG4. IgG1 is preferred.

The in vivo properties, particularly with regard to tumour-:blood ratio and rate of clearance, of specific binding members of the invention will be comparable to NHS76. Following administration to a human or animal subject such a specific binding member will show a peak tumour to blood ration of >3:1. Preferably at such a ratio the specific binding member will also have an organ to blood ratio of <1:1 in organs away from the site of the tumour. These ratios exclude organs of catabolism and secretion of the administered specific binding member. Thus in the case of scFvs and Fabs (as shown in the accompanying examples), the binding members are secreted via the kidneys and there is greater localisation here than other organs. In the case of whole IgGs, clearance will be at least in part, via the liver. The peak localisation ratio will normally be achieved between the 48 and 96 hours following administration of the specific binding member. More particularly, the ratio may be measured in a tumour xenograft of about 0.2–1.0 g formed subcutaneously in one flank of an athymic nude mouse.

Antibodies of the invention may be labelled with a detectable or functional label. Detectable labels include radiolabels such as $^{131}$I or $^{99}$Tc, which may be attached to antibodies of the invention using conventional chemistry known in the art of antibody imaging. Labels also include enzyme labels such as horseradish peroxidase. Labels further include chemical moieties such as biotin which may be detected via binding to a specific cognate detectable moiety, e.g. labelled avidin.

Functional labels include substances which are designed to be targeted to the site of a tumour to cause destruction of tumour tissue. Such functional labels include toxins such as ricin and enzymes such as bacterial carboxypeptidase or nitroreductase, which are capable of converting prodrugs into active drugs at the site of a tumour.

Antibodies of the present invention are designed to be used in methods of diagnosis and treatment of tumours in human or animal subjects, particularly solid tumours which have a necrotic centre. These tumours may be primary or secondary solid tumours of any type including, but not limited to, cervical, ovarian, prostate, lung, liver, pancreatic, colon and stomach tumours.

Antibodies of the present invention may be administered to a patient in need of treatment via any suitable route, usually by injection into the bloodstream or directly into the site of the tumour. The precise dose will depend upon a number of factors, including whether the antibody is for diagnosis or for treatment, the size and location of the tumour, the precise nature of the antibody (e.g. whole antibody, fragment or diabody), and the nature of the detectable or functional label attached to the antibody. Where a radio nuclide is used for therapy, a suitable maximum single dose is about 60 mCi/m$^2$, to a maximum of about 250 mCi/m$^2$. A typical antibody dose for either tumour imaging or tumour treatment will be in the range of from 0.5 to 40 mg, preferably from 1 to 4 mg of antibody in F(ab')$_2$ form. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician.

It is presently preferred that F(ab')$_2$ antibody fragments are used for both tumour imaging and tumour treatment.

Specific binding members of the present invention will usually be administered in the form of a pharmaceutical composition, which may comprise at least one component in addition to the specific binding member.

Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, anti-oxidants and/or other additives may be included, as required.

A composition may be administered alone or in combination with other treatments, either simultaneously or sequentially dependent upon the condition to be treated. Other treatments may include the administration of suitable doses of pain relief drugs such as non-steroidal anti-inflammatory drugs (e.g. aspirin, paracetamol, ibuprofen or ketoprofen) or opitates such as morphine, or anti-emetics.

The present invention further provides an isolated nucleic acid encoding a specific binding member of the present invention. Nucleic acid includes DNA and RNA. In a preferred aspect, the present invention provides a nucleic acid which codes for a polypeptide of the invention as defined above, including a polypeptide as set out as residues 99 to 106 of SEQ ID NO:2 or 88 to 98 of SEQ ID NO:4, and more preferably for the entire polypeptides of SEQ ID NO:2 and SEQ ID NO:4.

The present invention also provides constructs in the form of plasmids, vectors, transcription or expression cassettes which comprise least one polynucleotide as above.

The present invention also provides a recombinant host cell which comprises one or more constructs as above. A nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*.

The expression of antibodies and antibody fragments in prokaryotic cells such as *E. coli* is well established in the art. For a review, see for example Plückthun, A. Bio/Technology 9: 545–551 (1991). Expression in eukaryotic cells in culture is also available to those skilled in the art as an option for production of a specific binding member, see for recent reviews, for example Reff, M. E. (1993) Curr. Opinion Biotech. 4: 573–576; Trill J. J. et al. (1995) Curr. Opinion Biotech 6: 553–560.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a specific binding member or polypeptide as above.

The following examples illustrate the present invention.

EXAMPLE 1

Isolation of Antibodies Equivalent To TNT-1

1a. Preparation of Antigen

In order to generate clones specific for human nuclear antigens, the human Burkitt's lymphoma cell line, Raji, was used as a source of antigen, prepared largely as described by G. K. Miller et. al. 1993 Hybridoma vol.12, no.6 p.p. 689–697.

Cultures were grown in RPMI-1640+L-glutamine medium (Gibco BRL) supplemented with penicillin, streptomycin (Gibco BRL) and 5% foetal calf serum (FetalClone II, Hyclone Europe Ltd). Cells were grown in roller bottles and produced in 1 l batches. The culture was centrifuged at 1000 rpm for 10 min and the cells washed in PBS solution (Oxoid). The culture was spun again and the resultant pellet frozen down in 90% FCS/10% DMSO. Each 1 l batch gave 1.3–9.5×10⁸ cells.

To prepare nuclear extract, a cell pellet was first thawed on ice and gently resuspended in 10 ml 10 mM $CaCl_2$, 2 μM PIPES buffer. Cells were pelleted at 1000 rpm and resuspended in the same buffer containing 1% Nonidet P40. This was incubated on ice for 10 min to allow the disruption of the cell membrane. A small aliquot was removed and analysed by light microscopy. This indicated that no intact cells remained. Nuclei were pelleted by momentary centrifugation at 3000 rpm. The nuclei (pearly white pellet) were resuspended in 5 ml CaPIPES buffer. 1 ml nuclei were pelleted and resuspended in 1 ml sterile TE pH8.0. This was subjected to 3×45 sec sonication bursts to disrupt the nuclear membrane. Debris was pelleted at 13000 rpm (microfuge) for 2 min and the supernatant transferred to a fresh tube. The amount of nuclear extract was determined by absorption at 260 nm using the conversion factor $10A_{260}=1$ mg nucleohistone. The yield of nucleohistone was estimated to be 1.2 mg/ml.

1b. Induction of Phage Antibody Libraries

Two different phage antibody repertoires were selected for antibodies to Raji cell nuclear extract, the VH synthetic (Nissim et al., 1994) and large scFv' (Vaughan et al 1996) repertoires were each treated as follows in order to rescue phagemid particles. 500 ml prewarmed (37° C.) 2YTAG (2YT media supplemented with 100 μg/ml ampicillin and 2% glucose) in a 2 l conical flask was inoculated with approximately $3\times10^{10}$ cells from a glycerol stock (−70° C.) culture of the appropriate library. The culture was grown at 37° C. with good aeration until the OD600nm reached 0.7 (approximately 2 hours). M13K07 helper phage (Stratagene) was added to the culture to a multiplicity of infection (moi) of approximately 10 (assuming that an OD600nm of 1 is equivalent to $5\times10^{8}$ cells per ml of culture). The culture was incubated stationary at 37° C. for 15 minutes followed by 45 minutes with light aeration (200 rpm) at the same temperature. The culture was centrifuged and the supernatant drained from the cell pellet. The cells were resuspended in 500 ml 2YTAK (2YT media supplemented with 100 μg/ml ampicillin and 50 μg/ml kanamycin), and the culture incubated overnight at 30° C. with good aeration (300 rpm). Phage particles were purified and concentrated by a polyethylene glycol (PEG) precipitations (Sambrook et al., 1990) and resuspended in 10 ml 1×TE. 0.5 g/ml caesium chloride was added to each dissolved, transferred to ultracentrifuge tubes and centrifuged at 42000 rpm at 16° C. in a Sorvall TFT 65.13 rotor overnight. The caesium banded phage were removed with a needle and syringe and dialysed overnight in 2×2 l TE at 4° C. using a Slide-a Lyzer Cassette (Pierce) according to the manufacturers instructions. Phage were stored at 4° C. until use.

1c. Panning of Phage Antibody Library on Nuclear Extract

Phage induced from the two repertoires were each separately panned on Raji cell nuclear extract, the same antigen as that used for the inoculation of mice to give TNT-1. For the large scFv repertoire, $1\times10^{9}$ sub-aliquots of the library were selected separately. A 75 mm×12 mm immuno tube (Nunc; Maxisorp) was coated with 10 μg nuclear extract in 1 ml sterile PBS overnight at 4° C., followed by 1 hour at 37° C. After washing 3 times with PBS, the tube was filled with 3% MPBS (3% 'Marvel' skimmed milk powder, 1×PBS) and incubated for 1 hour at 37° C. for blocking. The wash was repeated, phagemid particles (1012 tu) in 2 ml of 3% MPBS were added and the tube incubated stationary at 37° C. for 1 hour. The tube was washed 10 times with PBST (0.1%), then 10 times with PBS. Bound phage particles were eluted from the tube by adding 1 ml of 100 mM-triethylamine, and incubating the tube stationary at room temperature for 10 minutes. The eluted material was immediately neutralised by pipetting into a tube containing 1 ml 1M-Tris.HCl (pH7.4). Phage were stored at 4° C. 1.5 ml of eluted phage were used to infect 10 ml of logarithmically growing *E. coli* TG1 (Gibson, 1984). Infected cells were grown for 1 hour at 37° C. with light aeration in 2YT broth, and then plated on 2YTAG medium in 243 mm×243 mm dishes (Nunc). Plates were incubated overnight at 30° C. Colonies were scraped off the plates into 10 ml of 2YT broth and 15% (v/v) glycerol added for storage at −70° C.

Glycerol stock cultures from the first round of panning of each of the two repertoires on nuclear extract were rescued using helper phage to derive phagemid particles for the second round of panning. 250 μl of glycerol stock was used to inoculate 50 ml 2YTAG broth, and incubated in a 250 ml conical flask at 37° C. with good aeration until the OD600 nm reached 0.7 (approximately 2 hours). M13K07 helper phage (moi=10) was added to the culture which was then incubated stationary at 37° C. for 15 minutes followed by 45 minutes with light aeration (200 rpm) at the same temperature. The culture was centrifuged and the supernatant drained from the cell pellet. The cells were resuspended in 50 ml prewarmed 2YTAK, and the culture incubated overnight at 30° C. with good aeration.

Phage induced from the first round of panning of each of the two repertoires, was selected a second time as described above. After extensive washing, bound phage were eluted from the tube using 1 ml of 100 mM-triethylamine, neutralised by the addition of 0.5 ml 1M-Tris.HCl (pH7.4) and infected into TG1 cells as before.

1d. Growth of Single Selected Clones for Immunoassay

Individual colonies from the second round selection were used to inoculate 100 μl 2YTAG into individual wells of 96 well tissue culture plates (Corning). Plates were incubated at 30° C. overnight with moderate shaking (200 rpm). Glycerol to 15% was added to each well and these master plates stored at −70° C. until ready for analysis.

1e. ELISA to Identify Nuclear Extract Binding scFv

Clones specific for nuclear extract were identified by ELISA, using scFv displayed on phage. Cells from the master plates were used to inoculate fresh 96 well tissue culture plates containing 100 μl 2YTAG per well. These plates were incubated at 37° C. for 6–8 hours or until the cells in the wells were growing logarithmically (OD600 0.2–1.0). M13K07 was added to each well to an moi of 10 and incubated stationary for 15 min then 45 min with gentle shaking (100 rpm), both at 37° C. The plates were centrifuged at 2000 rpm for 10 min and the supernatant eluted. Each cell pellet was resuspended in 100 μl 2YTAK and incubated at 30° C. overnight.

Each plate was centrifuged at 2000 rpm and the 100 μl supernatant from each well recovered and blocked in 20 μl 18% M6PBS (18% skimmed milk powder, 6×PBS), stationary at room temperature for 1 hour. Meanwhile, flexible microtitre plates which had been blocked overnight stationary at 4° C. with either 50 μl 2.5 μg/ml nuclear extract in PBS or 50 μl PBS alone (giving an uncoated control plate), were washed 3 times in PBS and blocked for 2 h stationary at 37° C. in 3MPBS. These plates were then washed three times with PBS and 50 μl preblocked phage added to each well of both the nuclear extract-coated or uncoated plate. The plates were incubated stationary at 37° C. for 1 h after which the phage were poured off. The plates were washed by incubating for 2 min in PBST three times followed by incubating for 2 min in PBS three times, all at room temperature.

To each well of both the nuclear extract-coated and the uncoated plate, 50 μl of a 1 in 10000 dilution of sheep anti-fd antibody (Pharmacia) in 3MPBS was added and the plates incubated at 37° C. stationary for 1 h. Each plate was washed as described above and 50 μl of a 1 in 5000 dilution donkey anti-sheep alkaline phosphatase conjugate (Sigma) in 3MPBS added and incubated stationary at 37° C. for 1 h. Plates were washed as described as above followed by two rinses in 0.9% NaCl. Alkaline phosphatase activity was visualised using the chromagenic substrate pNPP (Sigma). The absorbance signal generated by each clone was assessed by measuring the optical density at 405 nm using a microtitre plate reader.

Clones were chosen for further analysis if the ELISA signal generated on the nuclear extract-coated plate was at least double that on the uncoated plate. About 350 out of 700 clones analysed met the criteria set. Eighty six of these clones were selected for further characterisation.

1f. Specificity ELISA

Eighty six clones, identified as binding nuclear extract rather an uncoated well, were further analysed for fine specificity. Specificity ELISA's were carried out using scFv displayed on phage as described above. Microtitre plate wells were coated with 50 μl of either 5 μg/ml nuclear extract, 5 μg/ml histone H1 (Boehringer Mannheim), 100 μg/ml lysozyme or PBS (the uncoated well) at 4° C. overnight in PBS then 1 hour at 37° C. After preblocking both the phage and the microtitre plates, 50 μl blocked phage from each clone was added to a well coated with each antigen or an uncoated well. As above, alkaline phosphatase activity was visualised using either the chromagenic substrate pNPP (Sigma). Clones which were specific for nuclear extract and histone H1 but showed no cross-reaction with lysozyme or the uncoated well were analysed further. Clones were designated specific for nuclear extract and histone H1 if the ELISA signal generated on both antigens was at least five-fold greater than the signal on either lysozyme or on an uncoated well. TNT-1 binds both nuclear extract and histone H1 but not lysozyme. Twenty nine of the clones gave a binding profile similar to TNT-1 and were characterised further.

EXAMPLE 2

Western Blot Analysis

2a. Preparation of Soluble scFv

The twenty nine clones with a binding profile similar to TNT-1 were analysed for binding to nuclear extract components by Western blot analysis. Soluble scFv prepared from the periplasm of 50 ml culture was used for this. 2 ml overnight culture (grown at 30° C. in 2TYAG) was added to 50 ml 2TYA and incubated at 30° C. to OD600 0.6. IPTG was added to a final concentration of 1 mM and the culture grown overnight at 30° C. Cells were pelleted in 50 ml Falcon tubes and taken up in 5 ml ice-cold 50 mM Tris-Cl pH8, 20% Sucrose, 1 mM EDTA. The suspension was incubated on ice for 30 min then pellet at 8K for 20 min in a SM-24 rotor. The supernatant was used for the Western blot analysis.

2b. Casting of SDS-Polyacrylamide Gel

An SDS-Polyacrylamide gel was mounted in a Bio-Rad electrophoresis cell and 100 ml 2.5×SDS loading buffer added into the slot to create a spirit level surface. 200 ml nuclear extract sample was heated for 2 min at 90° C. in 1×SDS loading buffer with betamercaptoethanol and applied to the top of the 2.5×SDS loading buffer. The gel was run at 20 mA until the bromophenol blue dye front had passed through the bottom of the gel. The protein was blotted from the gel on to a PVDF Immobilon-P transfer membrane, using a Bio-Rad semi-dry transfer cell 24 V. The membrane was briefly washed in methanol and air dried. The membrane was sliced into approximately 3 mm strips.

2c. Western Blotting

The membrane strips from above were briefly washed in methanol then water. Each membrane strip was blocked in 5% Marvel/PBS/Tween for 45 min in a Costar reagent reservoir divided in to 12 individual wells. Periplasmic extract of each clone was preblocked in Marvel/PBS by adding 0.5 ml 18% Marvel, 6×PBS to 2.5 ml of periplasmic preparation and incubating for 15 min at room temperature. The preblocked antibodies were added to each strip and incubated at room temperature for 1 h. The strips were washed for 30 min with several changes of PBS/Tween then transferred to another reagent reservoir and washed with PBS 2×5 min. 1/100 diluted 9E10 anti-myc tag in 3% Marvel/PBS was added to the strips and incubated at room temperature for 1 h. The strips were washed for 30 min with several of changes PBS/Tween then transferred to another reagent reservoir and washed with PBS 2×5 min. 1/1000 diluted goat anti-mouse IgG peroxidase in 3% Marvel/PBS was added to the strips and incubated at room temperature for 1 h. The strips was washed for 1 h with several of changes PBS/Tween then transferred to another reagent reservoir and washed with PBS 2×5 min and saline 2×5 min. Each strip was washed briefly in water, transferred to a new reagent reservoir and developed using ECL (Amersham) according to the manufacturers instruction. The film was exposed to the strips for between 2 min and 16 h.

A second western blot of selected candidates on bovine histone H1 preps and nuclear extract was performed using a 20% PhastGel using the Pharmacia Phast Gel system essentially as above.

The western blot showed that a large number of the candidates had a binding profile close to the binding profile of TNT1, recognising histone H1 and histone H3 but also binding to some extent to the other core histones and to other non-identified proteins in the preparation. Seven clones had almost identical binding by western blot analysis as TNT-1, NHS 16, NHS 19, NHS 39, NHS 45, NHS 65, NHS 76 and NHS 86. These TNT-1 equivalent clones were chosen for further analysis. A further clone, NHS 22 was also chosen for further analysis, it has a similar ELISA profile to the other candidates but a different Western blot pattern.

Not all candidates showed a TNT1 like profile, some clones did not give a sufficient signal to determine any binding profile and other clones had a Western blot profile that was different from the TNT1 profile. It is infact surprising that so many of the clones have similar profiles to the TNT1 Western blot profile taking in to account the complexity of the starting antigen.

2d. Sequencinq of TNT-1 Equivalent ScFv Antibodies

The nucleotide sequence of the TNT-1 equivalent human scFv antibodies were determined by first using vector-specific primers to amplify the inserted DNA from each clone. Cells from an individual colony on a 2YTAG agar plate were used as the template for a polymerase chain reaction (PCR) amplification of the inserted DNA using the primers pUC19 reverse and fdtet sequence. pUC19 reverse has the sequence: 5' AGC GGA TAA CAA TTT CAC ACA GG 3' (SEQ ID NO:5). fdtet sequence has the sequence: 5' GTC GTC TTT CCA GAC GTT AGT 3' (SEQ ID NO:6). Amplification conditions consisted of 30 cycles of 94° C. for 1 min, 55° C. for 1 min and 72° C. for 2 min, followed by 10 min at 72° C. The PCR products were purified using a PCR Clean-up Kit (Promega) in to a final volume of 50 μl H₂O. Between 2 and 5 μl of each insert preparation was used as the template for sequencing using the Taq Dye-terminator cycle sequencing system (Applied Biosystems). The primers mycseq10 and PCR-L-Link were used to sequence the light chain of each clone and PCR-H-Link and pUC19 reverse to sequence the heavy chain. The sequences of these primers are as follows:

```
pUC19 reverse    5' AGC GGA TAA CAA TTT CAC ACA GG 3'  (SEQ ID NO: 7)

myc sequence 10  5' CTC TTC TGA GAT GAG TTT TTG 3'     (SEQ ID NO: 8)

PCR-H-Link       5' ACC GCC AGA GCC ACC TCC GCC 3'     (SEQ ID NO: 9)

PCR-L-Link       5' GGC GGA GGT GGC TCT GGC GGT 3'     (SEQ ID NO: 10)
```

2e. Sequence and Source of the TNT-1 Equivalent ScFv Antibodies

Eight different TNT-1 equivalent antibodies were isolated from the selections using the two libraries described above. A further clone, D3, was isolated by the epitope imprinting of chTNT-1 using nuclear extract as the source of antigen, much as described in Jespers et al, (1994), Biotechnology 12; 899–903. Each clone name, its origin and its heavy and light chain germline is given below. The sequences of NHS 76 VH and VL chains (SEQ ID NOs: 2 and 4) are shown in FIGS. 1 and 2.

| CLONE | LIBRARY SOURCE | VH GERMLINE | VL GERMLINE |
|---|---|---|---|
| NHS 16 | large scFv | DP 71 | DPL 16 |
| NHS 19 | large scFv | DP 75 | DPL 11 |
| NHS 22 | large scFv | DP 47 | L12a |
| NHS 39 | large scFv | DP 75/15 | DPL 11 |
| NHS 45 | large scFv | DP 46 | L12a |
| NHS 65 | large scFv | DP 7 | DPL 11 |
| NHS 76 | synthetic | DP 67 | DPL 16 |
| NHS 86 | large scFv | DP 47 | L12a |

There does not appear to be any correlation between the specificity of these eight clones and their sequence. A wide range of VH/VL combinations are utilised and the CDR regions are highly variable. It is therefore unlikely that antibodies with equivalent in vitro binding characteristics to TNT-1 could be predicted from their amino acid sequence.

EXAMPLE 3

Conversion of Candidates to Whole Antibody Format

Restriction digests, ligations, clonings and PCRs Restriction digests, ligations and cloning of DNAs were essentially as described (Sambrook et al., 1987). Each PCR of 50 μl contained 10 mM Tris HCl pH 8.85, 25 mM KCl, 5 mM (NH₄)₂SO₄, 2 mM MgSO₄, 250 μM dNTPs, 0.5 μM each primer, 1U PwoI DNA polymerase (Boehringer Mannheim) and appropriate amounts of template DNA. Each reaction mixture was subjected to 15–25 cycles of 94° C., 30 s; 50° C., 30 s; 72° C., 60 s.

Construction of Cell Line Expressing NHS76 IgG

For the construction of cell lines expressing human IgG1 antibodies the heavy and light chain variable domains from the NHS76 scFv expressing phage were cloned into mammalian expression vectors containing human IgG1 and human lambda constant domains respectively. To facilitate possible subsequent cloning of the VH and VL domains of NHS76 into a single expression vector necessitated deletion of internal BamHI sites. The restriction sites were removed by PCR-directed mutagenesis (Ho, S. N., Hunt, H. D., Horton, R. M., Pullen, J. K. and Pease, L. R. 1989 Gene 77, 51–59) using primers P54 (SEQ ID NO: 15)+P58 (SEQ ID NO: 17) and P57 (SEQ ID NO: 16)+P17 (SEQ ID NO: 13) for NHS76 VH, and primers P61 (SEQ ID NO: 20)+P60 (SEQ ID NO: 19) and P59 (SEQ ID NO: 18)+P45 (SEQ ID NO: 14) for NHS76 Vλ. All oligonucleotide primers of Example 3 are shown in Table 6. The PCR products of the expected sizes were joined in a second PCR using P54+P17 for VH, and P61+P45 for Vl. No changes in amino acid sequences resulted with the removal of the restriction sites. Heavy chain expression vector The NHS76 VH DNA amplified with P54 and P17 was joined by overlapping PCR to a 158 bp DNA fragment containing a signal sequence, splice sites and intron from M13VHPCR1 (Orlandi et al., 1989) using oligonucleotides P10 (SEQ ID NO: 11) and P17. The 539 bp PCR product was cut with HindIII and ApaI and cloned into HindIII-ApaI cut pGamma1 (obtained from Lonza). Ligated DNA was transformed into E. coli TG1 and ampicillin-resistant colonies screened. A plasmid with the correct insertion was identified and designated pNHS76γ1. Light chain expression vector The vector for the expression of lambda chains was a modified version of pMR15.1 (obtained from Lonza) where the Cκ DNA was replaced with human Cλ DNA and was designated pCλ. The NHS76 Vλ DNA amplified with P61 and P45 was joined by overlapping PCR to a 168 bp DNA fragment containing a signal sequence, splice sites and intron from M13VKPCR1 (Orlandi et al., 1989) using oligonucleotides P11 (SEQ ID NO: 12) and P45. The 529 bp PCR product was cut with BstBI and PacI and cloned into BstBI-PacI cut pCλ. Ligated DNA was transformed into E. coli TG1 and ampicillin-resistant colonies screened. A plasmid with the correct insertion was identified and designated pNHS76l.

NHS76 IgG Expression

NHS76 IgG was expressed in the mouse myeloma cell line NSO (ECACC 85110503). 45 μg of pNHS76γ1 and 15 μg pNHS76λ DNAs were linearised by digestion with PvuI, ethanol precipitated and dissolved in 100 μl water. 10⁷ NSO cells were washed in PBS, resuspended in 0.9 ml PBS, mixed with the vector DNA and held in ice for 5 min. The cells were then electroporated with 2 pulses of 1.5 kV at 3 μFd and incubated in ice for 10 min. The transfected cells were then added to 30 ml Dulbecco's modified Eagle's medium (DMEM) containing 2 mM glutamine and 10% dialysed foetal calf serum (FCS) as described by Bebbington et al. (1992) and 50 μl aliquots distributed into 6×96-well plates. 24 h later glutamine-free DMEM/10% FCS (Bebbington et al. 1992) was added to each well. Three to 6 weeks after transfection colonies were screened by ELISA for the ability to secrete human IgG. Wells of ELISA plates (Immulon 4, Dynatech) were coated in 50 mM sodium bicarbonate/carbonate pH 9.6 with 100 ng per well of goat anti-human IgG antibodies (Sera-Lab). Supernatant from wells containing transfected colonies was added to the wells in PBS containing 0.05% (v/v) Tween 20 (PBST) for 1 h.

The plates were washed 3 times with PBST and captured human IgG was detected with 100 µl 1:2000–1:5000 dilution horseradish peroxidase (HRP) conjugated goat anti-human lambda antibodies in PBST (Sera-Lab). After 30 min at room temperature the plates were washed 3×PBST and 100 µl OPD substrate added (50 µl). Reactions were stopped after 5–10 min by the addition of 50 µl 12.5% (v/v) sulphuric acid and the A 490 nm measured. Transfectants secreting the highest amounts of IgG were expanded for growth in glutamine-free medium in reduced FCS, in gammaglobulin-free FCS or no FCS. Cell lines were subsequently cloned by limiting dilution.

Purification of Antibodies

Human IgG1 antibodies were purified by protein A affinity chromatography. Supernatant from the growth of transfected NSO cells secreting NHS76 IgG was clarified by centrifugation and passage through a 0.22 µm filter. A protein A Sepharose column (HiTrap, Pharmacia) was equilibrated with PBS and the supernatant applied. The column was then washed with 10 column volumes of PBS and any bovine IgG present (from the foetal calf serum in the culture medium) removed by elution with 0.1 M sodium acetate pH 4.5. After further washing with PBS human IgG was eluted with 0.1 M sodium acetate pH 3.5. Eluted fractions were neutralised with 1 M Tris HCl pH 9.0 and protein containing fractions identified by measuring the absorbance at 280 nm. Antibody containing fractions were pooled and dialysed against PBS.

EXAMPLE 4

Digestion of Whole Antibodies

For the animal model, the candidates were tested as both whole antibodies and as F(ab')2 fragments. These were generated by limited pepsin digestion. A trial digest was set up for each antibody tested. The following were added to a 1.5 ml microfuge tube:

25 µl whole antibody in PBS

5 µl 1M sodium acetate buffer at either pH 3, 3.5, 4, 4.5, 5 or 5.5 pepsin at a final concentration of 10 µg pepsin/mg antibody (enzyme/substrate=1/100).

water to give a total volume of 50 µl

The digest was incubated at 37° C. and samples taken out after 1, 4, 8 and 16 hours. The reaction was stopped by adding 3M Tris-HCl pHB8.8 to a final concentration of 0.3 M and analysed on a 10–15% Phast gel (Pharmacia).

This gave the optimum digestion conditions for each antibody and was applied to the large-scale digests. Following digestion, the F(ab')2 fragment was purified on a 24 ml S200 FPLC column and eluted in the 14–16.5 ml fractions. These were pooled and concentrated to about 4 mg/ml in an Amicon Centriprep YM10.

EXAMPLE 5

Iodination of Antibodies

For the iodination, first the required number of screw top eppendorf tubes were coated with iodogen. Iodogen (Pierce) was dissolved at 1.2 mg/ml in chloroform, then a 1 in 10 dilution in chloroform made. 0.5 ml was added to each tube and carefully blown off the under N2. These could be stored in a desiccator at 4° C. for future use. To iodinate, 0.5 mg of protein was transferred to an iodogen tube on ice and made up to 0.5 ml with borate labelling buffer (100 ml 100 mM Borax, 100 ml 0.9% NaCl, pH to 8.5 with HCl; Filter Sterilised). An appropriate volume of Na125I (250 µCi–2.5 mCi) was added, mixed and left on ice for 10 minutes. Using a fine pasteur pipette, the whole reaction was transferred to the top of a PD-10 column (Pharmacia Biotech) which has been pre-blocked with 5% BSA/PBS and washed through 5 times with sterile PBS. 0.5 ml aliquots of sterile PBS were added sequentially to the top of the column and run through. Similar 0.5 ml aliquots were collected at the bottom of the tube. Each fraction was then be counted in a gamma counter. The iodinated protein usually comes out in fractions 6–7.

EXAMPLE 6

Biodistribution Studies

Figure 3B:
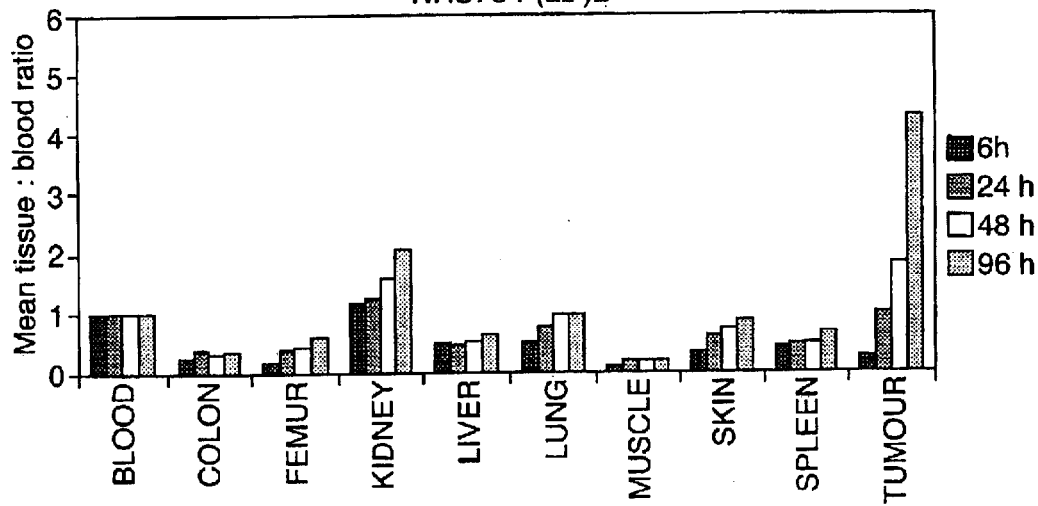

Experiments were conducted to establish the ability of F(ab')$_2$ fragments of NHS76 to localise to human tumour xenografts in athymic mice. Female athymic nu/nu MF-1 mice (4 per group) were injected subcutaneously with $10^7$ ME-180 human cervical carcinoma cells (ATCC HTB-33). Approximately 3–4 weeks later tumour-bearing mice were injected in the tail vein with 10 µg (37 kBq) $^{125}$I-labelled NHS76 IgG or $^{125}$I-labelled NHS76 F(ab')$_2$. At selected time points up to 96 h post-injection mice were sacrificed and blood, tumour and all major organs were collected and weighed (4 mice per time point). Radioactivity was measured in a gamma counter (Cobra II, Packard ). The percentage of the injected dose per gram of each organ was determined and the organ:blood ratios calculated. The ME-180 xenograft model is used in the art as an indicator for human clinical utility of test substances. See Epstein et al in "Handbook of Targeted Delivery of Imaging Agents", ibid. Table 1 and FIG. 3 show the biodistribution of $^{125}$I-labelled NHS76 F(ab')2. FIG. 3$a$ shows the distribution, and FIG. 3$b$ the mean tissue:blood ratio. The fragment is rapidly cleared from the circulation with only 1% of the injected dose remaining at 24 h p.i. NHS76 F(ab')2 demonstrates increased tumour localisation with time such that at 96 h p.i the tumour:blood ratio is 4.3:1. There is no specific retention in any other organ examined.

Figure 4A:
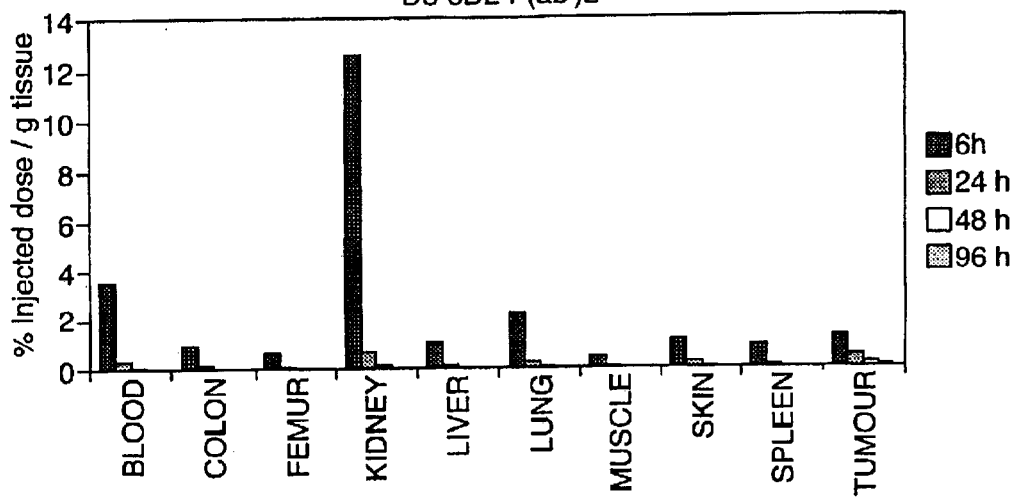
Figure 4B:
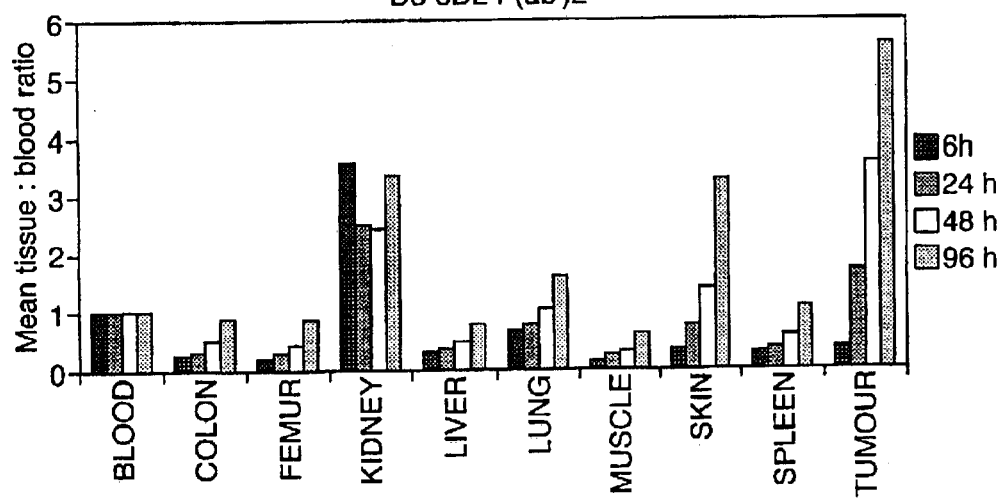

FIGS. 4$a$ and 4$b$ show the biodistribution and mean tumour:blood ratio respectively of 125I-labelled D3 F(ab')2. The data are shown in Table 2. D3 demonstrates a more rapid clearance from the circulation than NHS76 F(ab')2 with only 0.29% of the injected dose remaining in the circulation at 24 h. D3 F(ab')2 also shows specific tumour localisation and at 96 h shows a tumour:blood ratio of 5.6:1. There is also, however, retention of 125I in the skin (skin:blood ratio of 3.3:1). In comparison to NHS76, D3 demonstrates a much lower amount of accretion in tumour, for example at 96 h p.i. about there is about 6× less radioactivity in the tumour with D3 F(ab')2 than NHS76 F(ab')2.

Tables 3 and 4 show the biodistribution of 125I-labelled F(ab')2 fragments of NHS45 and NHS86. Both fragments are cleared from the circulation more rapidly than NHS76 F(ab')2 with 0.1% of the injected dose remaining at 24 h p.i. From 24 h to 96 h p.i. both antibody fragments show uptake to tumour and exhibit tumour:blood ratios of >3–5. However, fragments of both NHS45 and NHS86 also show significant retention in other organs.

NHS19 F(ab')2 shows little, if any, specific tumour uptake (Table 5, see also FIGS. 5$a$ and 5$b$).

Thus NHS76 F(ab')2, in contrast to the fragments of the other antibodies, shows the ability to localise to tumour with no specific retention in any other organ. The antigen binding specificity, the serum clearance and its entirely human makeup gives NHS76 F(ab')2 a composite of properties well suited for use in humans as an in vivo diagnostic or therapeutic agent with the potential for repeated administration.

TABLES 1–5 Biodistribution of 125I-labelled F(ab')2 fragments in ME-180 tumour-bearing athymic mice. Values represent the mean % injected dose (ID)/g; (SD of organs from 4–5 mice).

TABLE 1

NHS76 F(ab')2:% ID/g TISSUE

| ORGAN | Blood | Colon | Femur | Kidney | Liver | Lung | Muscle | Skin | Spleen | Tumour |
|---|---|---|---|---|---|---|---|---|---|---|
| 6 h | 7.96 | 1.95 | 1.41 | 9.08 | 3.97 | 3.89 | 0.73 | 2.59 | 3.47 | 1.99 |
|  | (0.38) | (0.18) | (0.20) | (0.92) | (0.27) | (0.24) | (0.13) | (0.40) | (0.18) | (0.40) |
| 24 h | 1.06 | 0.39 | 0.39 | 1.31 | 0.51 | 0.79 | 0.20 | 0.64 | 0.52 | 1.07 |
|  | (0.27) | (0.11) | (0.07) | (0.33) | (0.11) | (0.18) | (0.05) | (0.20) | (0.08) | (0.24) |
| 48 h | 0.20 | 0.07 | 0.08 | 0.32 | 0.11 | 0.20 | 0.04 | 0.15 | 0.10 | 0.38 |
|  | (0.04) | (0.01) | (0.02) | (0.05) | (0.02) | (0.03) | (0.01) | (0.02) | (0.02) | (0.05) |
| 96 h | 0.07 | 0.02 | 0.08 | 0.14 | 0.04 | 0.07 | 0.014 | 0.06 | 0.05 | 0.29 |
|  | (0.01) | (0.003) | (0.02) | (0.02) | (0.01) | (0.02) | (0.001) | (0.005) | (0.01) | (0.24) |

TABLE 2

D3 F(ab')2:% ID/g TISSUE

| ORGAN | Blood | Colon | Femur | Kidney | Liver | Lung | Muscle | Skin | Spleen | Tumour |
|---|---|---|---|---|---|---|---|---|---|---|
| 6 h | 3.51 | 0.92 | 0.61 | 12.6 | 1.06 | 2.24 | 0.48 | 1.13 | 0.94 | 1.24 |
|  | (0.23) | (0.07) | (0.09) | (3.2) | (0.06) | (0.82) | (0.17) | (0.25) | (0.10) | (0.40) |
| 24 h | 0.29 | 0.09 | 0.08 | 0.72 | 0.10 | 0.22 | 0.07 | 0.22 | 0.10 | 0.49 |
|  | (0.05) | (0.01) | (0.01) | (0.12) | (0.01) | (0.02) | (0.02) | (0.05) | (0.01) | (0.21) |
| 48 h | 0.04 | 0.02 | 0.02 | 0.10 | 0.02 | 0.04 | 0.01 | 0.06 | 0.02 | 0.14 |
|  | (0.02) | (0.01) | (0.005) | (0.05) | (0.01) | (0.02) | (0.003) | (0.01) | (0.01) | (0.11) |
| 96 h | 0.008 | 0.007 | 0.007 | 0.03 | 0.006 | 0.01 | 0.005 | 0.03 | 0.01 | 0.05 |
|  | (0.002) | (0.002) | (0.002) | (0.01) | (0.002) | (0.004) | (0.001) | (0.006) | (0.003) | (0.04) |

TABLE 5

NHS19 (Fab')2:% ID/g TISSUE

| ORGAN | Blood | Colon | Femur | Kidney | Liver | Lung | Muscle | Skin | Spleen | Tumour |
|---|---|---|---|---|---|---|---|---|---|---|
| 6 h | 0.74 | 0.41 | 0.33 | 1.36 | 0.40 | 0.53 | 0.19 | 0.63 | 0.35 | 0.51 |
|  | (0.16) | (0.22) | (0.26) | (0.21) | (0.08) | (0.15) | (0.13) | (0.29) | (0.10) | (0.11) |
| 24 h | 0.11 | 0.05 | 0.07 | 0.43 | 0.07 | 0.10 | 0.03 | 0.12 | 0.06 | 0.16 |
|  | (0.01) | (0.01) | (0.07) | (0.13) | (0.003) | (0.015) | (0.02) | (0.02) | (0.01) | (0.04) |
| 48 h | 0.07 | 0.04 | 0.03 | 0.25 | 0.05 | 0.06 | 0.02 | 0.09 | 0.04 | 0.11 |
|  | (0.03) | (0.01) | (0.008) | (0.07) | (0.02) | (0.02) | (0.003) | (0.04) | (0.01) | (0.04) |
| 96 h | 0.035 | 0.014 | 0.017 | 0.097 | 0.023 | 0.030 | 0.009 | 0.048 | 0.021 | 0.053 |
|  | (0.019) | (0.005) | (0.005) | (0.061) | (0.014) | (0.014) | (0.003) | (0.015) | (0.010) | (0.019) |

TABLE 3

NHS45 F(ab')2:% ID/g TISSUE

| ORGAN | Blood | Colon | Femur | Kidney | Liver | Lung | Muscle | Oesophagus | Skin | Small Intestine | Spleen | Stomach | Tumour |
|---|---|---|---|---|---|---|---|---|---|---|---|---|---|
| 6 h | 0.71 | 0.34 | 0.42 | 2.82 | 0.54 | 0.81 | 0.30 | 0.68 | 0.61 | 0.47 | 0.50 | 1.20 | 0.72 |
|  | (0.42) | (0.22) | (0.25) | (1.57) | (0.34) | (0.58) | (0.19) | (0.43) | (0.38) | (0.26) | (0.28) | (0.66) | (0.47) |
| 24 h | 0.10 | 0.08 | 0.09 | 0.30 | 0.15 | 0.15 | 0.04 | 0.19 | 0.23 | 0.10 | 0.12 | 0.19 | 0.23 |
|  | (0.005) | (0.02) | (0.02) | (0.05) | (0.04) | (0.02) | (0.01) | (0.09) | (0.06) | (0.02) | (0.03) | (0.06) | (0.03) |
| 48 h | 0.027 | 0.023 | 0.037 | 0.12 | 0.064 | 0.059 | 0.011 | 0.053 | 0.050 | 0.033 | 0.074 | 0.041 | 0.15 |
|  | (0.006) | (0.006) | (0.008) | (0.05) | (0.017) | (0.037) | (0.005) | (0.004) | (0.025) | (0.013) | (0.024) | (0.012) | (0.033) |
| 96 h | 0.007 | 0.012 | 0.020 | 0.028 | 0.013 | 0.016 | 0.005 | 0.049 | 0.020 | 0.019 | 0.027 | 0.011 | 0.026 |
|  | (0.003) | (0.003) | (0.005) | (0.017) | (0.008) | (0.007) | (0.001) | (0.011) | (0.005) | (0.008) | (0.016) | (0.001) | (0.014) |

TABLE 4

NHS86 F(ab')2:% ID/g TISSUE

| ORGAN | Blood | Colon | Femur | Kidney | Liver | Lung | Muscle | Oesophagus | Skin | Small Intestine | Spleen | Stomach | Tumour |
|---|---|---|---|---|---|---|---|---|---|---|---|---|---|
| 6 h | 1.62 | 1.07 | 1.51 | 6.45 | 5.23 | 2.58 | 0.85 | 1.56 | 1.66 | 2.57 | 3.57 | 3.47 | 1.75 |
|  | (0.42) | (0.22) | (0.25) | (1.57) | (0.34) | (0.58) | (0.19) | (0.43) | (0.38) | (0.26) | (0.28) | (0.66) | (0.47) |
| 24 h | 0.12 | 0.14 | 0.23 | 0.50 | 0.34 | 0.35 | 0.06 | 0.22 | 0.22 | 0.19 | 0.38 | 0.23 | 0.29 |
|  | (0.01) | (0.02) | (0.02) | (0.06) | (0.04) | (0.11) | (0.01) | (0.05) | (0.02) | (0.02) | (0.02) | (0.03) | (0.05) |
| 48 h | 0.072 | 0.067 | 0.12 | 0.28 | 0.13 | 0.19 | 0.029 | 0.19 | 0.12 | 0.099 | 0.22 | 0.091 | 0.25 |
|  | (0.032) | (0.027) | (0.04) | (0.10) | (0.04) | (0.09) | (0.007) | (0.11) | (0.02) | (0.029) | (0.13) | (0.041) | (0.07) |
| 96 h | 0.030 | 0.027 | 0.053 | 0.079 | 0.044 | 0.049 | 0.011 | 0.064 | 0.043 | 0.029 | 0.061 | 0.035 | 0.054 |
|  | (0.009) | (0.013) | (0.030) | (0.027) | (0.019) | (0.010) | (0.002) | (0.015) | (0.012) | (0.011) | (0.016) | (0.014) | (0.012) |

TABLE 6

OLIGONUCLEOTIDE PRIMERS

P10 5'-CTAAGCTTACTGAGCACACAGGACCTCACC-3'
P11 5'-AATTTTCGAACTACAGTTACTGAGCACACAGGACC-3'
p17 5'-ATGGGCCCTTGGTGGAAGCTGAAGAGACGGTGACCAGGGTGCC-3'
P45 5'-GCAAAGTTAATTAATTCTACTCCACCTAGGACGGTCAGCTTGGTCCCTCCGCCGAA-3'
P54 5'-TTTGGATATCTCTCCACAGGTGTCCACTCCCAGGTGCAGCTGCAGGAGTCCGGCCCA-3'
P57 5'-CTGGGGCTGGATTCGGCAGCCCCCA-3'
P58 5'-TGGGGGCTGCCGAATCCAGCCCCAG-3'
P59 5'-GCCCTCAGGGATTCCAGACCGATTC-3'
P60 5'-GAATCGGTCTGGAATCCCTGAGGGC-3'
P61 5'-TTGGATATCTCTCCACAGGTGTCCACTCCTCTTCTGAGCTGACTCAGGACCCT-3'

EXAMPLE 7

Antigen Specificity of NHS76

Figure 6:
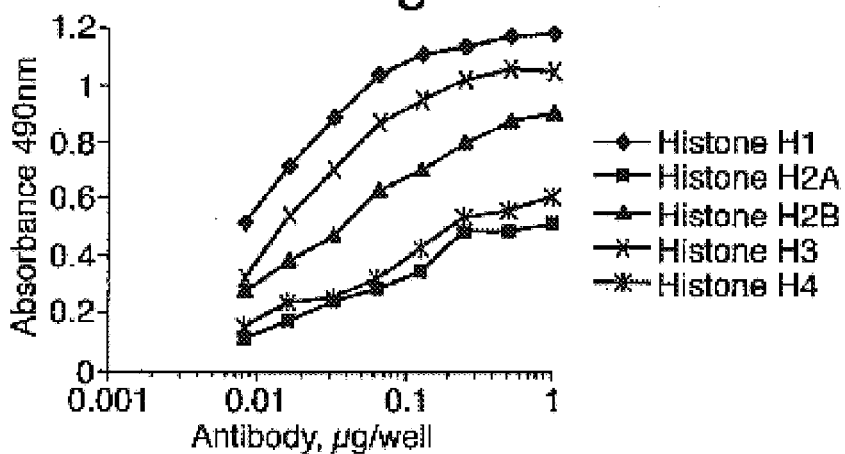

The ability of NHS76 IgG to bind to histones was examined by ELISA. Wells of microtitre plates (Immulon IV, Dynatech) were coated with 100 ng bovine histones (Boeringher Mannheim) in 50 mM bicarbonate/carbonate buffer pH9.6 at 4C for 16 h. Wells were blocked with 200 μl 2% Marvel in PBST (MPBST) for 1 h at 37C. After washing in PBST, NHS76 IgG in 100 μl MPBST was added to the wells and incubated for 1 h at room temperature. After washing, bound IgG was detected by the addition of 100 μl 1:2000 HRP goat anti-human IgG antibodies (Harlan Sera-Lab). After 30 min at room temperature the wells were washed and 100 μl o-phenylenediamine (0.4 mg/ml in 24 mM citric acid, 52 mM $Na_2HPO_4$ pH 5.2, 0.003% $H_2O_2$) added. After 6 min the reaction was stopped by the addition of 50 μl 12.5% sulphuric acid and the absorbance at 490 nm measured. The relative binding of the NHS76 IgG is histone H1>histone H3>histone H2B>histone H4=histone H2A (FIG. 6). A competition ELISA to determine the relative binding of NHS76 IgG to histones in solution was also employed and confirmed the ELISA data.

Figure 7A:
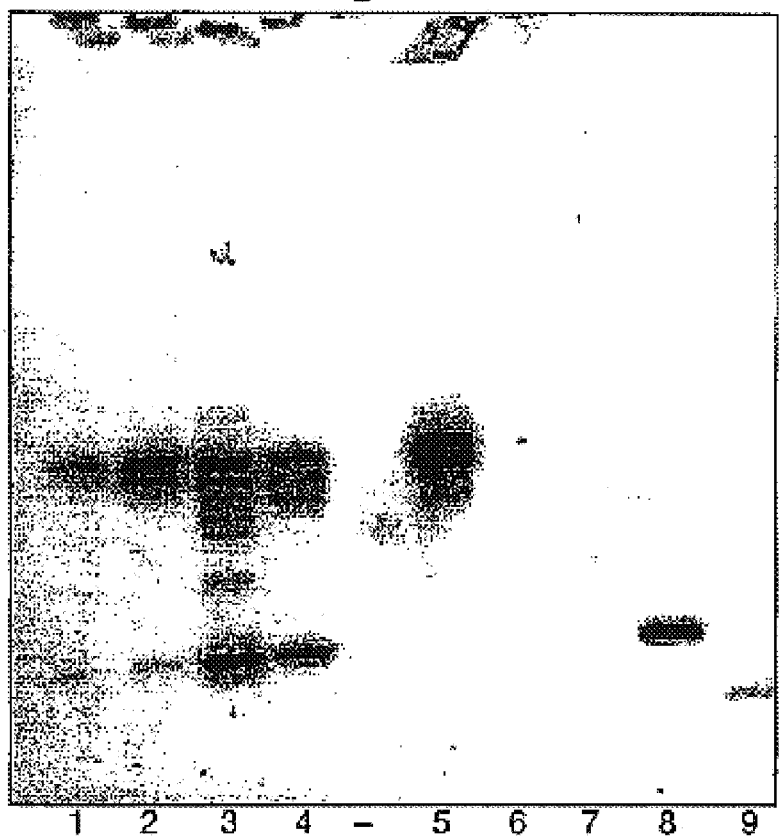
Figure 7B:
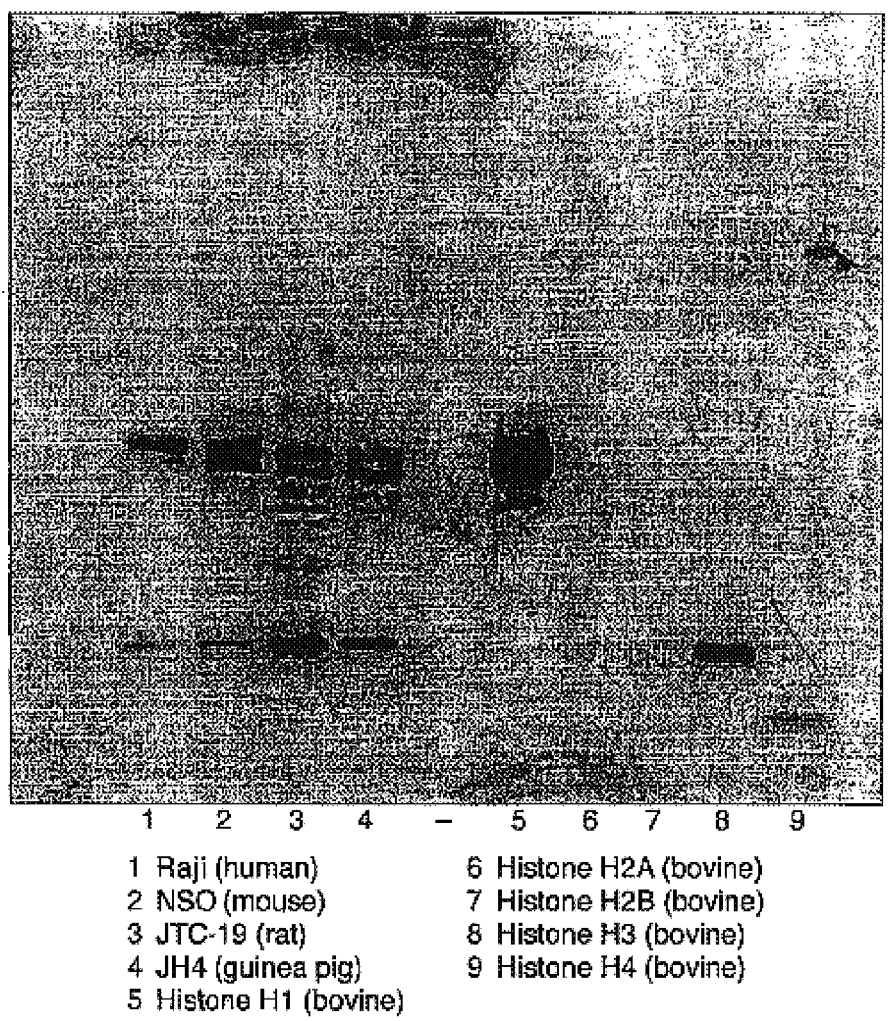

The ability of NHS76 IgG to bind histones from human and other species was analysed by Western blotting. Nuclear extracts of Raji (human), NSO (mouse), JTC-19 (rat) and JH4 (guinea pig) cells were electrophoresed through a reducing 14% SDS-PAG. The gel was electroblotted onto nitrocellulose membrane (Amersham International) which was subsequently blocked with MPBST for 1 h at room temperature. The membrane was then incubated with NHS76 IgG at 1 μg/ml for 50 min at room temperature. After 4 washes with PBST the membrane was incubated with 1:5000 HRP goat anti-human IgG in MPBST for 40 min at room temperature. After extensive washing the membrane was incubated with ECL reagent (Amersham) according to the manufacturer's instructions. The western blot result (FIGS. 7a–c (3 different exposures to show bands at different intensities)) demonstrates the binding of NHS76 IgG to proteins from human, mouse, rat and guinea pig cells which comigrate with bovine histones H1 and H3.

What is claimed is:

1. An antibody comprising a specific binding member capable of binding an intracellular antigen, wherein said specific binding member comprises a polypeptide binding domain comprising an amino acid sequence as set out as residues 99 to 106 of SEQ ID NO: 2.

2. An antibody comprising a specific binding member according to claim 1, which further comprises the polypeptide domains as set out as residues 31–36 and 51–66 of SEQ ID NO: 2.

3. An antibody comprising a specific binding member according to claim 2, wherein said binding domains are carried by a human antibody framework.

4. An antibody comprising a specific binding member according to claim 3, which comprises the polypeptide sequence of SEQ ID NO: 2.

5. An antibody comprising a specific binding member which comprises a first specific binding member comprising an amino acid sequence as set out as residues 99 to 106 of SEQ ID NO: 2 in association with a second specific binding member comprising an amino acid sequence as set out as residues 88 to 98 of SEQ ID NO: 4.

6. An antibody comprising a specific binding member which comprises a first specific binding member comprising an amino acid sequence as set out as residues 99 to 106 of SEQ ID NO: 2 in association with a second specific binding member comprising the polypeptide binding domains as set out as residues 23–33 and 49–55 of SEQ ID NO: 4.

7. An antibody comprising a specific binding member which comprises a first specific binding member comprising an amino acid sequence as set out as residues 99 to 106 of SEQ ID NO: 2 in association with a second specific binding member comprising the polypeptide sequence of SEQ ID NO: 4.

8. An antibody comprising a specific binding member which comprises a first specific binding member comprising an amino acid sequence as set out as residues 99 to 106 of SEQ ID NO: 2 in association with a second specific binding member comprising the polypeptide binding domains as set out as residues 23–33 and 49–55 of SEQ ID NO: 4, wherein said binding domains are carried by a human antibody framework.

9. An antibody comprising a specific binding member according to claim 8 in the form of an antibody F(ab')2 or scFv fragment.

10. An isolated nucleic acid which comprises a sequence encoding a specific binding member as defined in claim 1.

11. A method of preparing an antibody comprising a specific binding member that comprises a polypeptide binding domain comprising an amino acid sequence as set out as residues 99 to 106 of SEQ ID NO: 2, said method comprising the steps of expressing a nucleic acid which comprises a sequence encoding a specific binding member as defined in claim 1, and recovering the binding member.

12. A method of treatment or diagnosis of a tumor in a human or animal body comprising administering an antibody comprising a specific binding member according to claim 1.

13. A method of preparing an antibody comprising a specific binding member capable of binding an intracellular antigen, which method comprises:

a) providing a starting repertoire of nucleic acids encoding a VH domain which lacks a CDR3 encoding region;

b) combining said repertoire with a donor nucleic acid encoding an amino acid sequence as set out as residues 99 to 106 of SEQ ID NO: 2 such that said donor nucleic acid is inserted into the missing CDR3 region, so as to provide a product repertoire of nucleic acids encoding a VH domain;

c) expressing the nucleic acids of said product repertoire;

d) selecting a specific binding member which has a maximum tumor:blood localization ratio in a test animal of greater than 3:1; and e) recovering said binding member or the nucleic acid encoding said binding member.

14. A method of preparing an antibody comprising a specific binding member capable of binding an intracellular antigen, which method comprises:

a) providing a starting repertoire of nucleic acids encoding a VH domain which lacks a CDR3 encoding region;

b) combining said repertoire which a donor nucleic acid encoding an amino acid sequence as set out as residues 99 to 106 of SEQ ID NO: 2 such that said donor nucleic acid is inserted into the missing CDR3 region, so as to provide a product repertoire of nucleic acids encoding a VH domain;

c) expressing the nucleic acids of said product repertoire;

d) selecting a specific binding member which has a maximum tumor:blood localization ratio in a test animal of greater than 3:1, and at said ratio, has a minimum organ to blood ratio of less than 1:1; and e) recovering said binding member or the nucleic acid encoding said binding member.

15. A method of treatment of a tumor in a human patient which comprises administering to said patient an effective amount of an antibody comprising a specific binding member as defined in claim 1.

16. An antibody comprising a specific binding member which comprises a first specific binding member comprising an amino acid sequence as set out as residues 31–36, 51–66 and 99 to 106 of SEQ ID NO: 2 in association with a second specific binding member comprising an amino acid sequence as set out as residues 88 to 98 of SEQ ID NO: 4.

17. An antibody comprising a specific binding member according to claim 1, wherein said antibody carries a label selected from the group consisting of a detectable label and a functional label.

18. An antibody comprising a specific binding member according to claim 17, wherein said detectable label is selected from the group consisting of radiolabels, enzyme labels, chemical moieties bound to a specific cognate detectable moiety.

19. An antibody comprising a specific binding member according to claim 18, wherein said radiolabel is selected from the group consisting of $^{131}$I and $^{99}$Tc.

20. An antibody comprising a specific binding member according to claim 18, wherein said enzyme label is horseradish peroxidase.

21. An antibody comprising a specific binding member according to claim 18, wherein said chemical moieties bound to a specific cognate detectable moiety label is labeled avidin.

22. An antibody comprising a specific binding member according to claim 17, wherein said functional label is selected from the group consisting of toxins and enzymes capable of converting prodrugs into active drugs.

23. An antibody comprising a specific binding member according to claim 22, wherein said functional label is ricin.

24. An antibody comprising a specific binding member according to claim 22, wherein said functional label is carboxypeptidase.

25. An antibody comprising a specific binding member according to claim 22, wherein said functional label is nitroreductase.

* * * * *

UNITED STATES PATENT AND TRADEMARK OFFICE
CERTIFICATE OF CORRECTION

PATENT NO. : 6,827,925 B1 Page 1 of 1
DATED : December 7, 2004
INVENTOR(S) : Williams et al.

It is certified that error appears in the above-identified patent and that said Letters Patent is hereby corrected as shown below:

<u>Title page,</u>
Item [56], References Cited, OTHER PULBLICATIONS,
"Miller et al.," reference, after "TNT-1" insert -- and --.
"Database EMBL. PIRZ:" reference, after "EMBL" delete "." and insert -- , --.
"Desrues et al.," reference, delete "Monclonal" and insert -- Monoclonal --.

Signed and Sealed this

Twenty-eighth Day of March, 2006

JON W. DUDAS
*Director of the United States Patent and Trademark Office*